United States Patent [19]

Detsch

[11] 4,221,222
[45] Sep. 9, 1980

[54] MEDICAL CUTTING INSTRUMENT

[76] Inventor: Steven G. Detsch, 4146 Bryan St., Oceanside, Calif. 92054

[21] Appl. No.: 914,844

[22] Filed: Jun. 12, 1978

[51] Int. Cl.$^3$ .......................................... A61B 17/322
[52] U.S. Cl. .................... 128/305.5; 30/280; 128/304
[58] Field of Search ............... 128/304, 305, 305.5, 128/757; 30/280, 278; 99/588, 590, 584; 144/155

[56] References Cited

U.S. PATENT DOCUMENTS

| | | | |
|---|---|---|---|
| 435,632 | 9/1890 | Mohring | 30/280 |
| 467,188 | 1/1892 | McShane | 30/280 X |
| 2,876,777 | 3/1959 | Kees | 128/304 |
| 3,328,877 | 7/1967 | Brown | 30/280 X |
| 3,688,407 | 9/1972 | Paquette | 32/40 R |
| 3,934,591 | 1/1976 | Gleason | 128/305.5 |
| 4,038,986 | 8/1977 | Mahler | 128/305.5 |
| 4,098,278 | 7/1978 | Schwartz | 128/305.5 |

FOREIGN PATENT DOCUMENTS

| | | | |
|---|---|---|---|
| 145928 | 6/1931 | Switzerland | 30/280 |
| 246445 | 9/1947 | Switzerland | 30/280 |
| 605850 | 7/1948 | United Kingdom | 30/280 |

*Primary Examiner*—Kyle L. Howell
*Assistant Examiner*—Michael H. Thaler
*Attorney, Agent, or Firm*—Michael W. York

[57] ABSTRACT

A medical cutting instrument including an elongated member having one end thereof curved to permit the application of pressure from a finger. A cutting blade is associated with the curved portion of the elongated member to permit tissue to be cut at a precise depth and width. A cutting blade forms an integral part of the elongated member and is so shaped that a rearward pull on the elongated member serves to cause the blade to cut the tissue. The entire elongated member including the blade and curved portion are all made of material that is readily sterilizable without losing its temper so that the instrument can be resharpened and sterilized numerous times. The instrument is particularly useful in obtaining tissue grafts that can be used in dental surgery and the like.

11 Claims, 5 Drawing Figures

U.S. Patent  Sep. 9, 1980  4,221,222
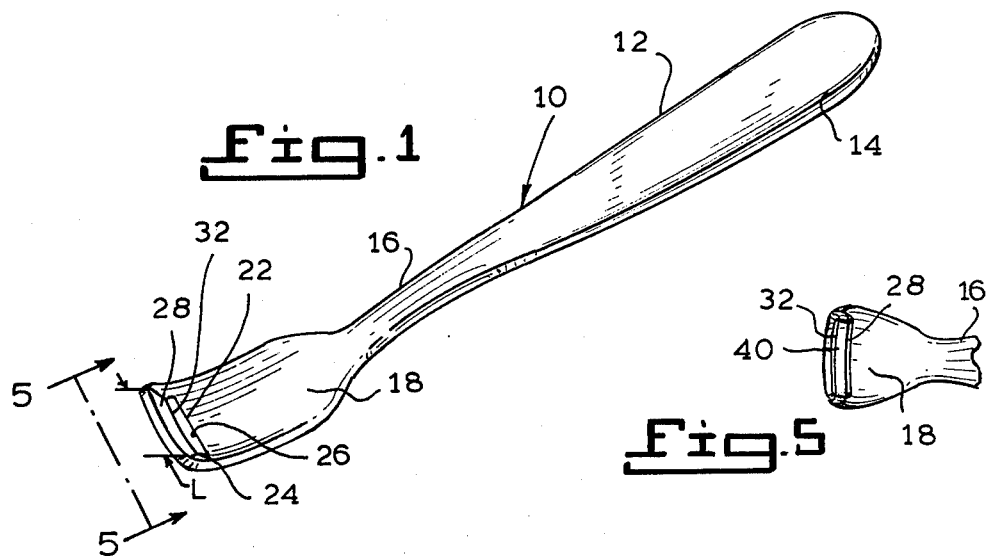
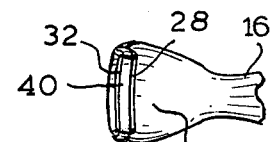
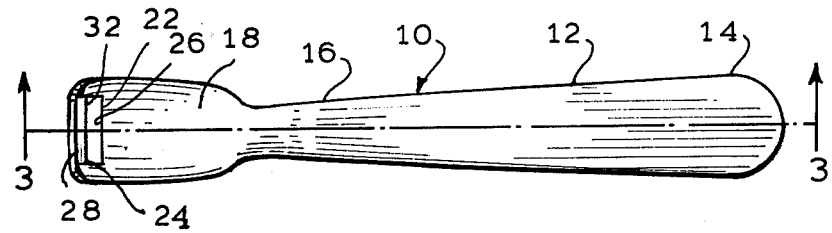
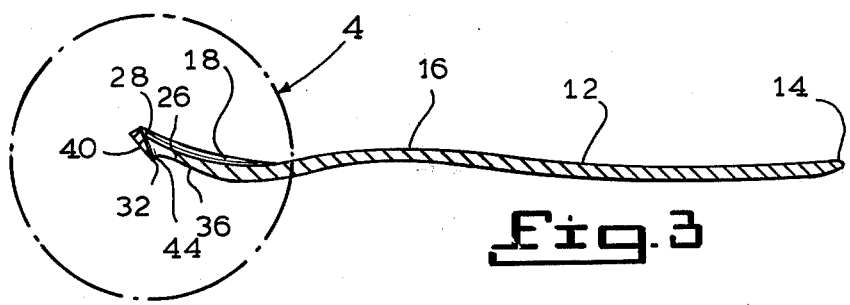
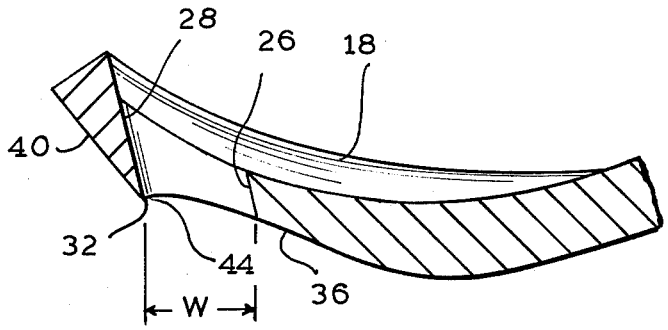

MEDICAL CUTTING INSTRUMENT

BACKGROUND OF THE INVENTION

The need to obtain living tissue for transplantation to portions of a human body has been recognized for many years. This has been particularly true with respect to the treatment of severe burns where the burned or damaged tissue had to be replaced by living tissue in order to permit the individual to properly recover. More recently it has been determined that deficient or defective gingival tissue can be replaced by tissue grafts that are taken from the mouth of the patient.

In the past there have been numerous cutting instruments that have been proposed for both medical and non-medical uses. Some of the early examples of such instruments are presented in U.S. Pat. No. 435,632, British Patent Number 605,850 and Swiss Patent Number 145,928. However, all of these patents disclose cutting instruments that have handles or other portions thereof that make them unsuitable for practical medical cutting use.

Other U.S. Pat. Nos. 3,688,407; 3,934,591 and 4,038,986 do disclose cutting instruments that are suitable for general medical use. However, none of the inventions disclosed in these patents enable the easy cutting of tissue of a precise width and depth without a great deal of skill on the part of the user of the instrument. Moreover, such inventions may require adjustments prior to their use and/or have blade portions thereof that are not readily reusable or resharpenable due to the fact that they cannot withstand certain types of sterilization.

This invention provides a simple medical cutting instrument that eliminates or greatly reduces the problems associated with the other cutting instruments set forth above. Moreover, the medical cutting instrument described herein is particularly useful for rapidly obtaining tissue that can be used for grafting and the like that has a particular width and depth.

SUMMARY OF THE INVENTION

This invention relates to medical cutting instruments for cutting tissue and more particularly to medical cutting instruments for cutting tissue of a particular thickness and depth.

It is an object of the present invention to provide a medical cutting instrument for rapidly cutting tissue.

It is an object of the present invention to provide a medical cutting instrument that is easily usable.

It is an object of the present invention to provide a medical cutting instrument which enables the easy procurement of a specific depth and width of tissue that is to be cut.

It is also an object of the present invention to provide a medical cutting instument that is readily reusable.

It is also an object of the present invention to provide a medical cutting instrument in which the width of the tissue to be cut is fixed.

It is also an object of the present invention to provide a medical cutting instrument in which the depth of the tissue to be cut is substantially fixed.

It is also an object of the present invention to provide a medical cutting instrument that is particularly useful in grafting tissue.

It is also an object of the present invention to provide a medical cutting instrument that is easy to resharpen.

It is also an object of the present invention to provide a medical cutting instrument which may be sterilized via usual procedures.

It is also an object of the present invention to provide a medical cutting instrument that can be readily used by one skilled in the art without any undue amount of special training.

The present invention provides a medical cutting instrument including cutting means for cutting living tissue and means associated with the cutting means for applying manual force to the cutting means. Additional means are also associated with the cutting means and the manual force applying means for substantially determining the depth of the living tissue that is to be cut. In addition, the width of the living tissue that is to be cut is also determined by the cutting means.

BRIEF DESCRIPTION OF THE DRAWINGS

The invention will be hereinafter more fully described with reference to the accompanying drawings in which:

FIG. 1 is a perspective view of the medical cutting instrument of the present invention;

FIG. 2 is a top plan view of the medical cutting instrument illustrated in FIG. 1;

FIG. 3 is a sectional view of the medical cutting instrument illustrated in FIG. 2 taken substantially on the line 3—3 thereof;

FIG. 4 is an enlarged view of a portion of the structure illustrated in FIG. 3 taken within the circle 4 thereof; and FIG. 5 is an end view of a portion of the medical cutting instrument illustrated in FIG. 1 taken in the direction of the line 5—5 thereof.

DETAILED DESCRIPTION OF THE PREFERRED EMBODIMENT

Referring first to FIGS. 1 through 3, the medical cutting instrument of the invention is illustrated and designated generally by the number 10. The medical cutting instrument 10 comprises a generally elongated member that has a handle portion generally designated by the number 12. This elongated handle portion is shaped or tapered so that the outer end thereof designated by the number 14 is larger than its inner portion designated by the number 16. As best illustrated in FIG. 2, the portion 16 is attached to a dish-shaped portion designated generally by the number 18.

The dish-shaped portion 18 is adapted to accept a finger of a person who is going to utilize the medical instrument designated generally by the number 10. In practicular, the portion designated to the number 18 is adapted to accept the curvature and the pressure of the finger of the like of a human being. This portion 18 is adapted to accept the pressure exerted by the human finger against the body tissue when the instrument 10 is in use.

Located immediately in front of the dish-shaped portion is a cutting portion designated generally by the number 22. This portion contains cutting means for cutting living tissue that is designated generally by the number 24. The portion 24 contains a blade member designated by the number 28 that is ground or otherwise formed into the upper side of the cutting portion 22 by means well known in the art. The slot 26 is so dimensioned that it substantially determines the cut of the tissue that is to be cut by the instrument 10. The slot designated by the number 26 contains the sharp portion 32 of the blade member 28. This sharp portion 32 generally faces in a direction toward the handle portion designated generally by the number 12 of the instrument 10.

The lower surface of the cutting portion designated generally by the number 22 has an under portion 36 as best illustrated in FIGS. 2 through 5 that permits the sharp portion 32 to make an appropriate cut in the living tissue. This is necessary so that when finger pressure is applied to the portion of the medical cutting instrument designated by the number 18 that the blade member and the sharp portion thereof 32 actually is pushed into intimate contact with the tissue that is to be cut. As best illustrated in FIGS. 2 through 4 an undercut portion 36 is located on the underside or on the opposite side of the finger rest portion 18. The forward portion 44 of this undercut portion has at least a portion thereof that terminates at the sharp cutting portion 32 and this permits the sharp cutting portion to cut into tissue.

As best illustrated in FIGS. 2 through 5, the cutting portion designated generally by the number 22 has a generally curved shaped surface 40 that has the sharp cutting portion 32 located at the end of this surface 40 that is located closest to finger rest portion 18. Also as best illustrated in FIG. 1 in the preferred embodiment the length L of the blade member sharp portion designated by the number 32 should be substantially between the dimensions 4 mm to 15 mm, with substantially 6 mm being the preferred, and as best illustrated in FIG. 4 the width W should be substantially between the dimensions 1 mm to 6 mm, with 3 mm being preferred. Furthermore, in the preferred embodiment the slot designated by the number 26 should as best illustrated in FIG. 1 have a length substantially equal to L for the blade member 28 or the sharp portion 32 and as best illustrated in FIG. 4 a width W of substantially between the dimensions 1 mm to 6 mm, with 2 mm being preferred.

The entire instrument 10 should be made from material that is capable of surviving multiple thermal sterilizations and also the blade portion designated by the number 28 whould be thick enough so that it can be repeatedly resharpened to be sure that it is adequate for surgical use.

The medical cutting instrument designated generally by the number 10 is utilized in the following manner. The dish-shaped cutting portion 22 is placed against the tissue donor site so that the cutting means 24 is located immediately adjacent to the tissue that is to be cut. Pressure is then exerted against the portion designated by the number 18. In the preferred embodiment this pressure is applied through the use of the finger of a surgeon or some other appropriately trained individual. This results in the sharp portion 32 of the blade member 28 being forced into the living tissue. While pressure is continuously applied to the portion designated by the number 18, the instrument 10 is pulled rearward or toward its end designated by the number 14 so that the sharp portion 32 of the blade member 28 is pulled through the tissue of the donor site.

The width of the blade member sharp portion 32 determines the width of the graft that is taken. When an adequate length of tissue graft has been taken the surgeon or other appropriately trained person then draws the blade member portion upward to free the tissue graft from the donor site. The tissue that is obtained from the donor site is then applied to the graft site in a conventional manner that is well known in the art.

The medical cutting instrument designated by the number 10 is particularly useful as a gingival microtome which is particularly useful for simplifying the removal of gingival graft tissue from donor sites. For instance, experiments have indicated that graft removal time could be lessened from upwards of 15 minutes to fifteen seconds. Consequently, the instrument 10 should make it possible for a surgeon or other medically qualified individual to obtain a graft of uniform width and thickness with great ease. Moreover, it has been determined that the blade portion 28 of the instrument 10 is easy to sharpen which would lessen the technician's work time and eliminate the need for and the cost of disposable blades that are currently in use. Furthermore, experiments have indicated that the graft tissue that has been yielded from the use of the instrument 10 has resulted in an almost completely smooth tissue base and a uniform thickness. Improved wound healing of gingival grafts and donor sites have been demonstrated using this invention.

It should be realized that the shape of the handle 12 and the finger rest portion 18 and the blade shape and width are easily varied to suit the surgeon or other qualified individual's surgical needs.

The instrument 10 is very easy to sharpen and it can be repestedly easily resharpened by even a comparatively untrained technician. Sharpening or resharpening of the instrument 10 is easily accomplished by merely removing a portion of the surface 40 to cause the portion 32 to be sharpened or resharpened. This is easily accomplished by touching the surface 40 to an appropriate sharpening wheel that is known in the art.

Although the invention has been described in considerable detail with reference to a certain preferred embodiment, it will be understood that variations and modifications may be made within the spirit and scope of the invention as defined in the appended claims.

What is claimed is:

1. A gingival microtome for removing gingival graft tissue from donor sites comprising an elongated handle having an outer end and an inner end portion, a pressure exerting portion connected to the inner end portion of said elongated handle, said pressure exerting portion comprising a concave dish-shaped portion adapted to accept the curvature and pressure of a human finger or the like when said gingival microtome is in use, said pressure exerting portion having a curved surface shaped to generally conform to the shape of the tissue in the vicinity of the tissue that is to be cut, and a cutting portion located adjacent to said pressure exerting portion, said cutting portion having a slot and a curved blade member having a sharp cutting portion located adjacent to the slot in said cutting portion, said cutting portion having an undercut under portion with at least a portion thereof that terminates at the sharp cutting portion of said blade member, said blade member having the sharp cutting portion thereof facing generally in a direction toward said elongated handle, the cutting portion of said blade member being substantially perpendicular to the long axis of said elongated handle, said concave dish-shaped portion being positioned immediately above the pressure exerting portion and extending forwardly into the slot.

2. The gingival microtome of claim 1 wherein the length of the slot in said cutting portion is substantially equal to the length of the sharp cutting portion of said blade member.

3. The gingival microtome of claim 1 wherein the width of the slot in said cutting portion is substantially between 1 mm to 6 mm.

4. The gingival microtome of claim 3 wherein the width of the slot in said cutting portion is substantially 3 mm.

5. The gingival microtome of claim 1 wherein the length of the sharp cutting portion of said blade member is substantially between 4 mm to 15 mm.

6. The gingival microtome of claim 1 wherein said blade member forms an integral part of said gingival microtome.

7. The gingival microtome of claim 1 wherein said gingival microtome is made from a material capable of surviving multiple thermal sterilizations.

8. The gingival microtome of claim 1 wherein said cutting portion has an exterior sharpening surface.

9. The gingival microtome of claim 8 wherein said gingival microtome has two end portions and the sharpening surface of said cutting portion is located at one of said end portions.

10. The gingival microtome of claim 9 wherein the cross section of said blade member is wedge shaped.

11. The gingival microtome of claim 10 wherein said elongated handle is tapered so that the outer end portion thereof is larger than the inner portion thereof.

* * * * *